United States Patent
BeMiller et al.

(10) Patent No.: US 7,598,374 B2
(45) Date of Patent: Oct. 6, 2009

(54) PROCESSES FOR THE PRODUCTION OF XYLITOL

(75) Inventors: James N. BeMiller, West Lafayette, IN (US); Jonathan A. Stapley, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 592 days.

(21) Appl. No.: 11/093,091

(22) Filed: Mar. 25, 2005

(65) Prior Publication Data

US 2005/0272961 A1 Dec. 8, 2005

Related U.S. Application Data

(60) Provisional application No. 60/556,571, filed on Mar. 26, 2004.

(51) Int. Cl.
C07H 1/00 (2006.01)
C07C 29/14 (2006.01)

(52) U.S. Cl. ........................ 536/124; 568/864

(58) Field of Classification Search ................ 536/124; 568/864

See application file for complete search history.

(56) References Cited

U.S. PATENT DOCUMENTS

| | | | |
|---|---|---|---|
| 2,852,567 A * | 9/1958 | Barnard et al. ............... | 568/801 |
| 2,989,569 A | 6/1961 | Apel | |
| 3,558,725 A | 1/1971 | Kohno et al. | |
| 3,619,369 A | 11/1971 | Onishi et al. | |
| 3,627,636 A | 12/1971 | Jaffe et al. | |
| 3,784,408 A | 1/1974 | Jaffe et al. | |
| 3,980,719 A | 9/1976 | Buckl et al. | |
| 3,992,268 A * | 11/1976 | Antos ......................... | 205/462 |
| 4,008,285 A | 2/1977 | Melaja et al. | |
| 4,066,711 A | 1/1978 | Melaja et al. | |
| 4,075,406 A | 2/1978 | Melaja et al. | |
| 4,125,559 A | 11/1978 | Scholz et al. | |
| 4,429,140 A | 1/1984 | Murai et al. | |
| 4,617,090 A * | 10/1986 | Chum et al. ................. | 162/16 |
| 4,742,814 A | 5/1988 | Sinner et al. | |
| 4,950,366 A | 8/1990 | Jiricny et al. | |
| 5,045,340 A | 9/1991 | Kohler et al. | |
| 5,081,026 A | 1/1992 | Heikkila et al. | |
| 5,096,820 A | 3/1992 | Leleu et al. | |
| 5,162,517 A | 11/1992 | Darsow et al. | |
| 5,536,526 A | 7/1996 | Virtanen et al. | |
| 5,563,303 A | 10/1996 | Vuorinen et al. | |
| 5,616,361 A | 4/1997 | Virtanen et al. | |
| 5,631,150 A | 5/1997 | Harkki et al. | |
| 5,686,277 A | 11/1997 | Kim et al. | |
| 5,714,602 A | 2/1998 | Beck et al. | |
| 5,831,078 A | 11/1998 | Elseviers et al. | |
| 5,998,181 A | 12/1999 | Kim et al. | |
| 5,998,607 A | 12/1999 | Heikkila et al. | |
| 5,998,608 A | 12/1999 | Tamion | |
| 6,221,634 B1 | 4/2001 | Takeuchi et al. | |
| 6,245,940 B1 | 6/2001 | Tamion | |
| 6,271,007 B1 | 8/2001 | Apajalahti et al. | |
| 6,303,353 B1 | 10/2001 | Sugiyama et al. | |
| 6,335,177 B1 | 1/2002 | Mihara et al. | |
| 6,340,582 B1 | 1/2002 | Suzuki et al. | |
| 6,458,570 B1 | 10/2002 | Elseviers et al. | |
| 6,476,217 B1 | 11/2002 | Tamion | |
| 6,538,133 B1 | 3/2003 | Aoki et al. | |
| 6,723,540 B1 | 4/2004 | Harkki et al. | |
| 6,764,706 B1 | 7/2004 | Heikkila et al. | |
| 6,846,657 B2 | 1/2005 | Heikkila et al. | |
| 2002/0076772 A1 | 6/2002 | Elseviers et al. | |
| 2002/0164731 A1 | 11/2002 | Eroma et al. | |
| 2003/0068791 A1 | 4/2003 | Miasnikov et al. | |
| 2003/0097029 A1 | 5/2003 | Heikkila et al. | |
| 2003/0125588 A1 | 7/2003 | Heikkila et al. | |
| 2003/0235881 A1 | 12/2003 | Heikkila et al. | |
| 2004/0002054 A1 * | 1/2004 | Horvitz et al. .................. | 435/4 |
| 2004/0014185 A1 | 1/2004 | Ojamo et al. | |
| 2004/0132074 A1 | 7/2004 | Verho et al. | |
| 2004/0142456 A1 | 7/2004 | Jeffries et al. | |
| 2004/0191881 A1 | 9/2004 | Raj et al. | |

FOREIGN PATENT DOCUMENTS

| | | |
|---|---|---|
| CN | 1381585 A | 11/2002 |
| CZ | 274 796 | 2/1990 |
| DE | 102 58 089 A1 | 6/2004 |
| EP | 0 421 882 A2 | 4/1991 |

(Continued)

OTHER PUBLICATIONS

U.S. Appl. No. 10/341,220, filed Jan. 2003, Ojamo.

(Continued)

*Primary Examiner*—Shaojia Anna Jiang
*Assistant Examiner*—Everett White
(74) *Attorney, Agent, or Firm*—Brinks Hofer Gilson & Lione (57) ABSTRACT

Methods of producing xylitol comprising the oxidative decarboxylation of a reactant substrate are provided herein. The oxidative decarboxylation is performed in one of two ways. In the first, the oxidative decarboxylation is performed by an electrochemical process, preferably an anodic odixative decarboxylation of a reactant substrate. In the second, the oxidative decarboxylation of the reactant substrate is carried out by a series of oxidation-reduction chemical reactions.

14 Claims, 6 Drawing Sheets

FOREIGN PATENT DOCUMENTS

| | | |
|---|---|---|
| EP | 0 421 882 A3 | 4/1991 |
| JP | 57-128697 | 8/1982 |
| JP | 58-039695 | 3/1983 |
| JP | 2004-24140 A | 1/2004 |
| WO | WO 02/06504 A1 | 1/2002 |
| WO | WO 02/088154 A1 | 11/2002 |
| WO | WO 02/088155 A1 | 11/2002 |
| WO | WO 03/097848 A1 | 11/2003 |
| WO | WO 2004/048559 A1 | 6/2004 |
| WO | WO 2004/052813 A1 | 6/2004 |
| WO | WO 2004/085627 A1 | 10/2004 |
| WO | WO 2004/108739 A2 | 12/2004 |
| WO | WO 2005/010171 A1 | 2/2005 |

OTHER PUBLICATIONS

Bragd, P.L. et al.; Selective Oxidation of Carbohydrates by 4-AcNH-TEMPO/peracid Systems; Carbohydrate Polymers 49; pp. 397-406; 2002.

De Faveri, D., et al., Optimization of xylitol recovery by crystallization from synthetic solutions using response surface methodology. Journal of Food Enginering, vol. 61, 407-412 (2004).

Jiřičný, V. et al.; Preparation of D-arabinose in a Laboratory Fluidized Bed Electrode Cell; Collect. Czech. Chem. Commun. vol. 60; pp. 863-874; 1995.

Jiřičný, V. et al.; Production of D-arabinose in a Pilot Plant Fluidized Bed Electrochemical Reactor; Journal of Applied Electrochemistry 24; pp. 930-935; 1994.

Kochetkov, N.K., et al., Selective cleavage of glycuronosidic linkages. Carbohydrate Research, vol. 14, 277-285 (1970).

Matsuoka, K., et al., Anodic oxidation of polyhydric alcohols on a Pt electrode in alkaline solution. Fuel Cells (Weinheim, Germany) 2, 35-39 (2002).

Pergola, F., et al., Direct electro-oxidation of D-gluconic acid to D-arabinose. Electrochimica Acta 39, 1415-1417 (1994).

Pezzatini, G., et al., Electro-oxidative decarboxylation of D-gluconic acid to D-arabinose on graphite electrodes. Electroanlaysis, vol. 4, 129-132 (1992).

Schuurman, Y., et al., Selective oxidation of methyl α-D-glucoside on carbon supported platinum. In "New Developments in Selective Oxidation by Heterogeneous Catalysis", Ruiz, P.; and Delmon, B., eds., vol. 72 of "Studies in Surface Science and Catalysis", 1992, pp. 43-55.

Schuurman, Y., et al., Selective oxidation of methyl α-D-glucoside on carbon supported platinum. II. Assessment of the Arrhenius and Langmuir parameters. Applied Catalysis A: General, vol. 89, 31-46 (1992).

Schuurman, Y., et al., Selective oxidation of methyl α-D-glucoside on carbon supported platinum. III. Catalyst deactivation. Applied Catalysis A: General, vol. 89, 47-68 (1992).

Taylor, R.L. Sorbitol from glucose by electrolytic reduction. Chemical and Metallurgical Engineering, vol. 44, 588-591 (1937).

Vallieres, C., and Matlosz, M., A multisectioned porous electrode for synthesis of D-arabinose. Journal of the Electrochemical Society 146, 2933-2939 (1999).

International Search Report for International Application No. PCT/US05/10377.

Emil Fischer and Otto Ruff, "On the conversion of gulonic acid to xylose and galactose," *Berichte der Deutschen Chemischen Gesellschaft*, 33:2142-2147 (1900).

Carl Neuberg, "Electrolysis in the Sugar Series," *Biochemische Zeitschrift*, 7:537-538 (1908).

Joseph Kiss, Richard D'Souza and Paul Taschner, "Preparative production of 5-deoxy-L-arabinose, xylitol and D-ribose from 'giacetone glucose'," *Helvetica Chimica Acta* 58:311-317 (1975).

* cited by examiner

PROCESSES FOR THE PRODUCTION OF XYLITOL

This application claims the benefit of U.S. Provisional Application No. 60/556,571, "Processes for the Production of Xylitol," filed Mar. 26, 2004, which is incorporated herein by reference in its entirety.

TECHNICAL FIELD

The present invention relates to processes for the production of xylitol. In particular, the invention provides processes for the production of xylitol comprising the oxidative decarboxylation of compounds.

BACKGROUND

Xylitol is a naturally occurring five-carbon sugar alcohol present in many fruits and vegetables and produced in the human body during normal metabolism. Xylitol is also an important industrial product and is widely used in the production of confectionary products, including sugarless chewing gum, breath mints and dry hard candies, as well as in dental care products, health promoting products, pharmaceutical products and the like.

Certain characteristics of xylitol make it an attractive sweetener or sugar substitute in various contexts, particularly in the production of sweetened food products. For example, xylitol is non-toxic and has approximately the same sweetness as sucrose with a lower caloric content of about 2.4 kcal/g. Xylitol is metabolised independently of glucose and can be safely consumed by non-insulin dependent diabetics, has a very low glycemic index, and is reported to have an anti-ketogenic effect in diabetes. Xylitol crystals have an endothermic heat of solution and produce a cool feeling when dissolved in the mouth. Xylitol is also believed to be cariostatic and even anti-cariogenic, and is believed to not be utilized by the microflora of the mouth that produce plaques. Indeed, the use of xylitol in place of sucrose has been linked to a reduction in dental carries. Overall, xylitol is a desirable sweetener.

Xylitol is usually prepared by processes utilizing various natural raw materials, especially xylan-containing materials. Xylitol may be obtained by a variety of processes, including the hydrogenation of xylose that is isolated from a hemicellulose (xylan or arabinoxylan) hydrolyzate, as disclosed in U.S. Pat. Nos. 2,989,569, 3,558,725, and 4,008,285.

Catalytic hydrogenation of D-xylose in hemicellulose hydrolyzates remains the primary industrial source of xylitol. Industrial production of D-xylose is primarily performed by hydrolysis of hemicellulose (xylans and arabinoxylans). However, many of these processes for the production of xylitol are expensive or time-consuming, and a variety of alternative xylitol synthesis methods have been proposed. These include various synthetic chemical processes, the use of microorganisms, and processes such as fermentation. However, despite these developments, a need exists to produce xylitol in a manner that is low cost and yields high-purity product. A decrease in the waste produced during its production is also desirable. In view of the increasing use of xylitol, in particular due to its properties as sweetener and therapeutic effects, there is a continuing need for methods for the production of xylitol.

SUMMARY

Methods of producing xylitol comprising the oxidative decarboxylation of a reactant substrate are provided. Preferably, the oxidative decarboxylation is performed in one of two ways. In a first embodiment, the oxidative decarboxylation is performed by an electrochemical process, preferably an anodic odixative decarboxylation of a reactant substrate. In a second embodiment, the oxidative decarboxylation of the reactant substrate is carried out by a one or more chemical reactions.

A wide variety of reactant substrates can be used to practice the methods of producing xylitol. The reactant substrate can be a starting material for an oxidative decarboxylation reaction, or can be produced from any suitable precursor material. Preferred precursor materials are uronic acids comprising a pyranose or furanose ring structure. In some aspects of the embodiments, one or more precursor materials can undergo one or more chemical reactions, such as oxidation reactions, reduction reactions, or hydrolytic reactions, to produce a suitable reactant substrate.

Figure 1:
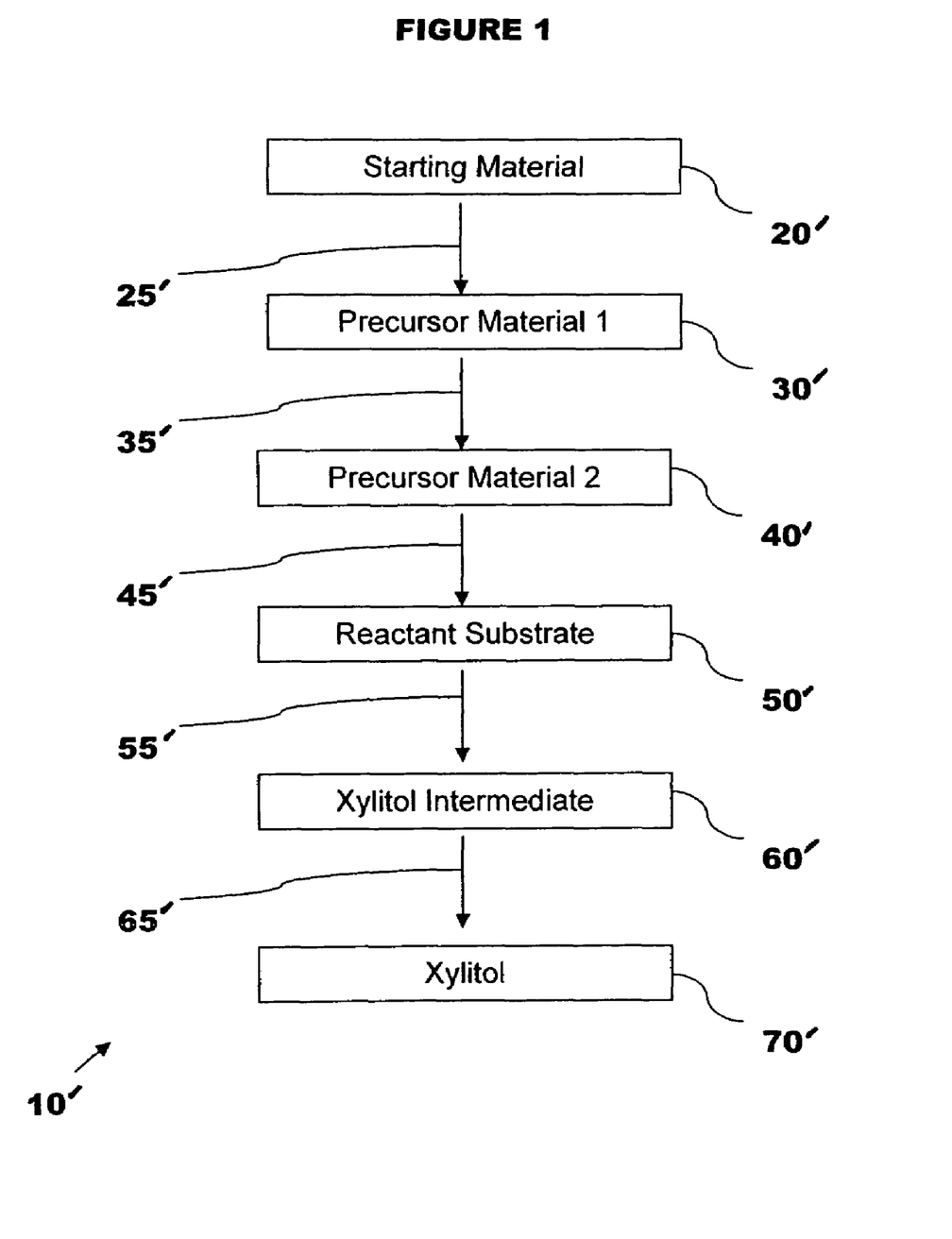
FIG. 1 shows a general reaction process for xylitol synthesis.

FIG. 1 shows a general reaction scheme 10' for producing xylitol according to some embodiments. The reaction scheme 10' comprises the steps of providing a reactant substrate 50' comprising a uronic acid moiety and oxidatively decarboxylating 55' the reactant substrate. Suitable reactant substrates include uronic acid containing reactant substrates that undergo a desired decarboxylation reaction under certain reaction conditions. In one embodiment, the method for preparing xylitol comprises the steps of providing a reactant substrate 50' comprising a uronic acid moiety and oxidatively decarboxylating 55' the reactant substrate by electrochemical oxidative decarboxylation of a suitable reactant substrate. Preferably, the reactant substrate comprises a uronic acid moiety in a pyranose or furanose ring structure. In an alternative embodiment, the method for preparing xylitol comprises the steps of providing a reactant substrate 50' comprising a uronic acid moiety and oxidatively decarboxylating 55' the reactant substrate by chemical oxidative decarboxylation of a suitable reactant substrate. Preferably, the reactant substrate of the second embodiment comprises a L-gulonic acid moiety.

The oxidative decarboxylation step 55' produces a xylitol intermediate compound 60', or alternatively produces xylitol or another compound useful in the production of xylitol. Various xylitol intermediate compounds can be produced, and the xylitol intermediate compounds produced according to the first embodiment may be the same or different from the xylitol intermediate compounds produced according to the processes of according to the second embodiment. The reactant substrate may be provided 50' as a starting material, or may be obtained from one or more precursor materials.

In FIG. 1, the method for producing xylitol 10' further comprises the steps of: provising a starting material 20', chemically modifying 25' the starting material 20' to obtain a first precursor material 30', chemically modifying 35' the first precursor material 30 to obtain a second precursor material 40' and chemically modifying 45' the second precursor material 40' to obtain the reactant substrate 50. The xylitol intermediate 60' is chemically modified 65' to produce a reaction product comprising xylitol 70'. Preferably, the reaction product comprises xylitol in a yield of at least 20% theoretical yield of xylitol. Chemical modification of a starting material, a precursor material, or a xylitol intermediate can indicate any suitable reaction or series of reactions that modify the chemical structure of the material, including oxidation reactions, reduction reactions, hydrolysis or condensation reactions.

In one preferred aspect of the first embodiment, a method of producing xylitol comprises the step of electrochemical oxidative decarboxylation of a D-glucuronic acid reactant substrate, a D-fructofuranosyl uronic acid reactant substrate or a L-gulonic acid reactant substrate to produce a xylitol intermediate. Preferably, method comprises the step of oxidatively decarboxylating a reactant substrate by anodic decarboxylation, where the reactant substrate is selected from the group consisting of: a glycoside, an oligosaccharide, a polysaccharide, 1-phosphate or a glycosyl fluoride of D-glucuronic acid salt. The oxidative decarboxylation step produces a xylitol intermediate compound. The xylitol intermediate is preferably a dialdehyde or dicarbonyl structure, that is preferably subsequently reduced with a hydrogenation catalyst and hydrogen gas to yield a product comprising xylitol.

In one preferred aspect of the second embodiment, a method of producing xylitol comprises the step of oxidative decarboxylation of a D-glucuronic acid reactant substrate to produce a dialdehyde xylitol intermediate, such as D-xylopent-1,5-diose. The oxidative decarboxylation step produces a first xylitol intermediate compound, preferably a dialdehyde or dicarbonyl structure. In another preferred aspect of the second embodiment, a method of producing xylitol comprises the step of oxidative decarboxylation of a L-gulonic acid reactant substrate, to produce a xylitol intermediate such as L-xylose, to produce a second xylitol intermediate, preferably a dialdehyde or dicarbonyl structure. Preferably, in all aspects of the second embodiment, a xylitol intermediate is further chemically modified, for example by a reduction/dehydrogenation reaction, to produce a reaction product comprising xylitol.

DETAILED DESCRIPTION OF PREFERRED EMBODIMENTS

The terms "about" or "substantially" used with reference to a quantity refer to variations in the recited quantity that are equivalent to the quantity recited, for instance an amount that is insubstantially different from a recited quantity for an intended purpose or function. Variation of a quantity or relationship modified by terms "about" or "substantially" include variations based on the general guidelines contained in the specification as read by one of ordinary skill in the art.

References to a "D-fructuronofuranosyl acid compound," and "D-glucuronopyranosyl acid compound," as used herein, include glycosides, polymers or oligomers and derivatives and salts thereof, unless otherwise specified.

Reference to a "D-glucuronic acid compound," as used herein, includes glycosides, polymers or oligomers thereof, preferably with a protected reducing end, and derivatives and salts thereof.

Reference to a "glucopyranose compound," as used herein, includes glycosides, polymers or oligomers of α(alpha)-, β(beta)- and α,β(alpha,beta)-glucopyranose, and derivatives and salts thereof.

Reference to a "fructofuranose compound," as used herein, includes glycosides, polymers or oligomers of α(alpha)-, β(beta)- and α,β(alpha,beta)-fructofuranose, and derivatives and salts thereof.

Reference to a "glucopyranosiduronic acid compound," as used herein, includes glycosides, polymers or oligomers of α(alpha)-, β(beta)- and α,β(alpha,beta)-(alpha,beta)-glucopyranosiduronic acid, and derivatives and salts thereof.

The term "starting material" refers to a chemical entity that is initially provided in a method for producing xylitol, prior to an oxidative decarboxylation reaction. A starting material can be chemically modified to produce a precursor material, or can be a reactant substrate for an oxidative decarboxylation reaction.

The term "precursor material" refers to the product of chemical modification of a starting material or the product of the chemical modification of another precursor material.

The term "reactant substrate" refers to a chemical entity that undergoes oxidative decarboxylation to produce a xylitol intermediate or a xylitol product. In some aspects, the starting material can also be a reactant substrate. A "uronic acid reactant substrate" is a reactant substrate that comprises at least one uronic acid moiety.

The term "uronic acid compound," as used herein, refers to a compound comprising a uronic acid, including certain glycosides, polymers or oligomers thereof, as well as corresponding salts thereof. A uronic acid compound, or derivatives and salts thereof, is preferably capable of being converted to a dialdehyde intermediate of xylitol, or derivatives and salts thereof.

Xylitol Synthesis Comprising Electrochemical Oxidative Decarboxylation

Figure 2:
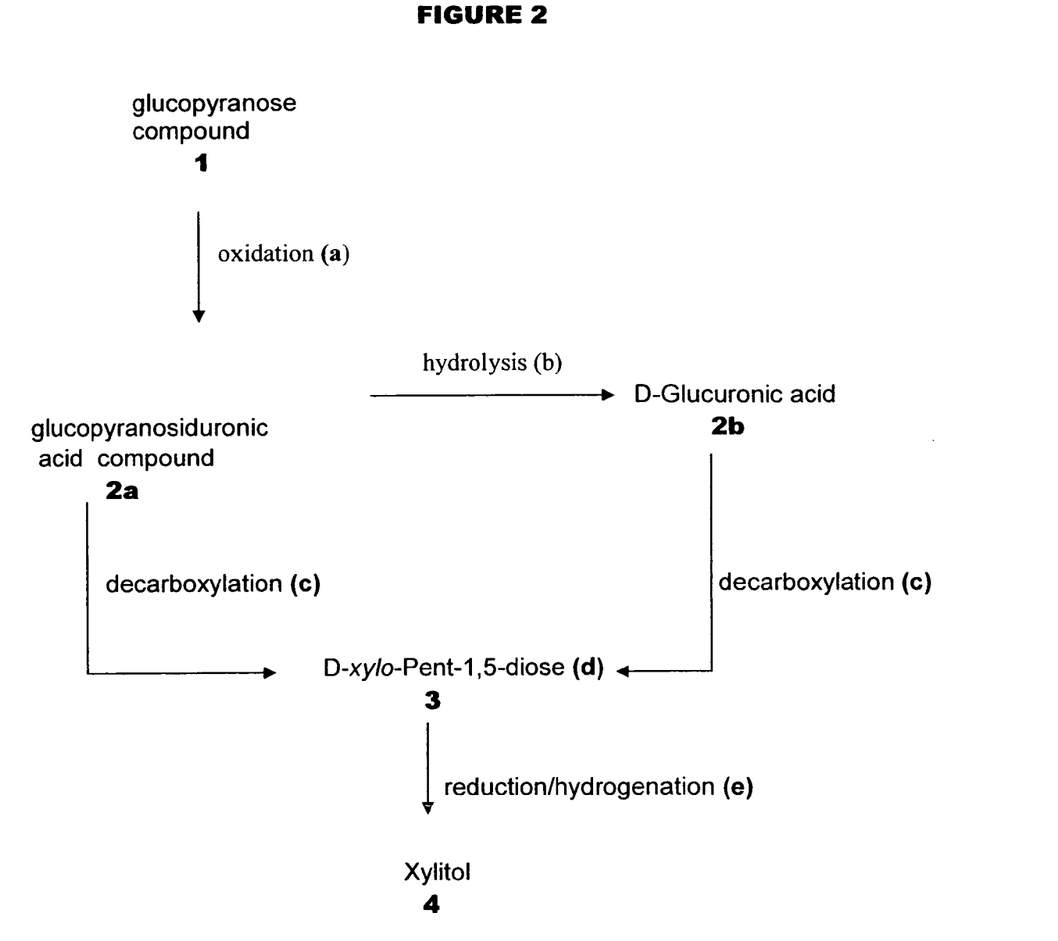
FIG. 2 shows two reaction processes for xylitol synthesis comprising an electrochemical odixative decarboxylation.

In a first embodiment, shown schematically in FIG. 2, processes for producing xylitol comprise an oxidative decarboxylation step performed by an electrochemical means, preferably by an odixative decarboxylation of a reactant substrate. The use of electrochemical decarboxylation in a xylitol synthesis has many advantages. In particular, few chemical reagents are involved and the reaction is capable of being highly selective, so it is often simpler to purify the product. Furthermore, there is typically a minimal waste stream, byproducts are negligible, and there are typically minimal spent reagents after electrochemical decarboxylation processes.

A glucopyranose compound (1) is used as a starting material for both processes shown in FIG. 2, although any starting material that can be converted to a suitable reactant substrate can be used as a starting material or a precursor material. The glucopyranose compound (1) can be oxidized (a) to a glucopyranosiduronic acid compound (2a) by any suitable oxidation reaction method to form a preferred reactant substrate. A starting material or precursor material can comprise any D-glucuronopyranosyl group that is not substituted at the oxygen in the 6-position, or D-fructuronofuranosyl group that is not substituted at the oxygen in the ring position. The reactant substrate (2a) is preferably a salt of D-glucuronic acid or a glycoside, oligomer or polymer thereof, either as a natural material or produced by an oxidation reaction (a). The reactant substrate (2a) can optionally be provided in the form of a sodium, potassium, ammonium, calcium, and/or magnesium salt.

The oxidation reaction (a) of the precursor material (1) to a reactant substrate may be accomplished by methods known in the art, including, but not limited to: air/$O_2$ oxidation on a catalyst such as platinum, stable nitroxyl radicals (e.g., TEMPO with regeneration), transition metal ion oxidation with electrochemical regeneration, and electrochemically. Suitable oxidation reactions (a) for use in oxidizing a D-glucopyranoyl compounds to D-glucuronopyranosyl units are described in the following references, which are incorporated herein by reference in their entirety: K. Heyns et al, "Selective catalytic oxidation of carbohydrates, employing platinum catalysts," *Advances in Carbohydrate Chemistry and Biochemistry,* 17, 169-221 (1962); T. Yamada et al., Air oxidation of cyclodextrin with a platinum catalyst," *Journal of Applied Glycoscience,* 47, 21-26 (2002); P. L. Bragd et al., "Selective oxidation of carbohydrates by 4-AcNH-TEMPO/peracid systems," *Carbohydrate Polymers,* 49, 397-406 (2002); K. Yasuda et al., "The simultaneous use of immobilized reagents for the one-pot conversion of alcohols to carboxylic acids," *Journal of the Chemical Society,* Perkin Transactions, 1, 1024-1025 (2002).

The glucopyranosiduronic acid (2a) can be used as a reactant substrate that undergoes electrochemical decarboxylation (c) to form a xylitol intermediate (3). Alternatively, the glucopyranosiduronic acid (2a) can be used as a precursor material that undergoes hydrolysis (b) to form a D-glucuronic acid (2b) reactant substrate. Hydrolysis (b) of the glucopyranosiduronic acid compound may be performed using an α- and/or β-glucuronosidase (or a mixture of both) or an acid with heat to release D-glucuronic acid. Glucuronic acid may be separated from any non-ionic saccharides by ion-exchange chromatography or electrodialysis. In either reaction method, a carboxyl-moiety on the reactant substrate (e.g., the glucopyranosiduronic acid compound (2a) or the D-glucuronic acid (2b)) reactant substrate undergoes electrochemical decarboxylation (c) to form a xylitol intermediate (3). The xylitol intermediate produced by both processes shown in FIG. 2 comprises D-xylo-pent-1,5-diose (d). Preferably, the xylitol intermediate (3) is a dialdehydo xylitol intermediate Suitable reactant substrates for performing the step of electrochemically oxidatively decarboxylating (c) a reactant substrate preferably contain a uronic acid that is preferably in a pyranose or furanose ring structure. A reactant substrate can be a carbohydrate acid such as an aldonic or saccharinic acid, although reactant substrates comprising a uronic acid are preferred. More specifically, a reactant substrate preferably comprises a chemical moiety selected from the group consisting of: a glycoside, an oligosaccharide, a polysaccharide, 1-phosphate or a glycosyl fluoride of D-glucuronic acid salt and a D-fructuronofuranosyl acid salt. Examples of preferred reactant substrates are shown in FIG. 2 as a glucopyranosiduronic acid compound (2a) or a D-glucuronic acid compound (2b).

The step of oxidative decarboxylation of a reactant substrate (c) is preferably performed by an electrochemical oxidative decarboxylation of the reactant substrate. The reactant substrate is preferably in its ionized (i.e., salt) form, either as a free compound or linked glycosidically to an alcohol or another molecule. A suitable oxidative decarboxylation (c) reaction to yield the xylitol intermediate (3) is an oxidative decarboxylation reaction, such as the Hofer-Moest reaction (Hofer and Moest, Annalen, 1902, 828, 284). The Hofer-Moest reaction is described, for example, by Kruis and Schanzer, *Z. physikal. Chem.,* 1942, 191, A, 301. Neuberg (Biochemische Zeitschrift 7 (1908) 537). The decarboxylation of D-gluconic acid to D-arabinose has been researched as an economically important reaction, and continuous flow reactors for the process have been developed. The following references are incorporated herein by reference in their entirety: Pergola et al., Electrochimica Acta 39 (1994) 1415; Pezzatini et al. Electroanalysis 4 (1992) 129; and Vallieres and Matlosz, Journal of the Electrochemical Society 146 (1999) 2933.

An apparatus for the decarboxylation of a reactant substrate preferably comprises an electrochemical cell. An anodic oxidative decarboxylation reaction (c) can be performed using the electrochemical cell. The electrochemical cell anode may be formed from any suitable material, but preferably spectroscopic graphite, pyrolytic carbon, wax-impregnated graphite, glassy carbon, dispersed graphite, dispersed carbonaceous material, carbon cloth, coke, or platinum as a packed bed, fluidized bed, or porous anode. U.S. Pat. No. 4,950,366, which is incorporated by reference in its entirety, discloses an apparatus for the decarboxylation of D-gluconic acid to yield D-arabinose that can be used to perform the oxidative decarboxylation reaction (c). The electrochemical cell preferably comprises an electrochemical cell anode, where the oxidative decarboxylation reaction (c) is believed to occur. The anode surface area is preferably large and can be made of many carbonaceous materials, platinum, or other metals. Contact between the starting material and the anode elicits the decarboxylation, which results in liberation of carbon dioxide and formation of the xylitol intermediate (3). Preferably, the electrochemical cell further comprises a cathode, where a reduction can occur within the electrochemical cell.

The electrochemical oxidative decarboxylation is believed to occur when a solution comprising a reactant substrate is contacted with the anode of an electrochemical cell to which a potential is applied. Without being bound by theory, it is believed that decarboxylation of a glucopyranosiduronic acid compound results in formation at carbon 5 of a carbocation (carbonium ion), which is stabilized as a carboxonium ion (involving the ring oxygen atom). Addition of a hydroxide ion or water molecule to this intermediate can form a hemiacetal, which in an aqueous environment opens, forming an aldehyde (carbon 5) and a hemiacetal at carbon 1. The later decomposes to an aldehyde, forming the dialdehyde.

Other examples of electrochemical oxidation methods are described in the following references, which are incorporated herein by reference in their entirety: Schuurman et al., Studies in Surface Science and Catalysis, 72 (1992) 43; Applied Catalysis A: General 89 (1992) 31, 47 and references therein; P. L. Bragd, A. C. Besemer, and H. van Bekkum, Carbohydrate Polymers 49 (2002) 397-406); Matsuoka et al., Fuel Cells 2 (2002) 35.

Performing the electrochemical decarboxylation (c) of a reactant substrate, such as glucopyranosiduronic acid (2a) or D-glucuronic acid (2b), yields a xylitol intermediate (3) such as D-xylo-pent-1,5-diose (d). One or more subsequent chemical modifications of the xylitol intermediate (3), such as a reduction-hydrogenation reaction (e) yields a product composition comprising xylitol (4). The non-ionic xylitol intermediate (3) may be separated from unreacted starting material (2), for example by anion-exchange chromatography or electrodialysis. Reduction of the xylitol intermediate (3) may be performed by any suitable method known in the art, including, but not limited to, catalytic hydrogenation. Effective catalysts include ruthenium and nickel. In particular, supported ruthenium catalysts and Raney nickel may be used. In one aspect, the xylitol intermediate (3) may be reduced with hydrogen and a ruthenium (WO Patent Appl. No. 2004052813, incorporated in its entirety herein by reference), nickel (U.S. Pat. No. 4,008,285, incorporated in its entirety herein by reference), or other known hydrogenation catalyst to produce xylitol (4). The hydrogenation is routinely performed at temperatures between about 70° C. and about 150°

C. and at pressures between about 0.1 and about 10 MPa $H_2$. Alternatively, electrochemical reduction may be used (Taylor, Chemical and Metallurgical Engineering, Vol. 44 (1937) 588, incorporated in its entirety herein by reference). Reduction of the intermediate obtained by decarboxylation of D-fructuronofuranosyl acid yields a mixture of xylitol and D-arabinitol. Xylitol can be recovered by crystallization (De Faveri et al., Journal of Food Engineering 61 (2004) 407, incorporated herein by reference in the entirety).

Figure 3:
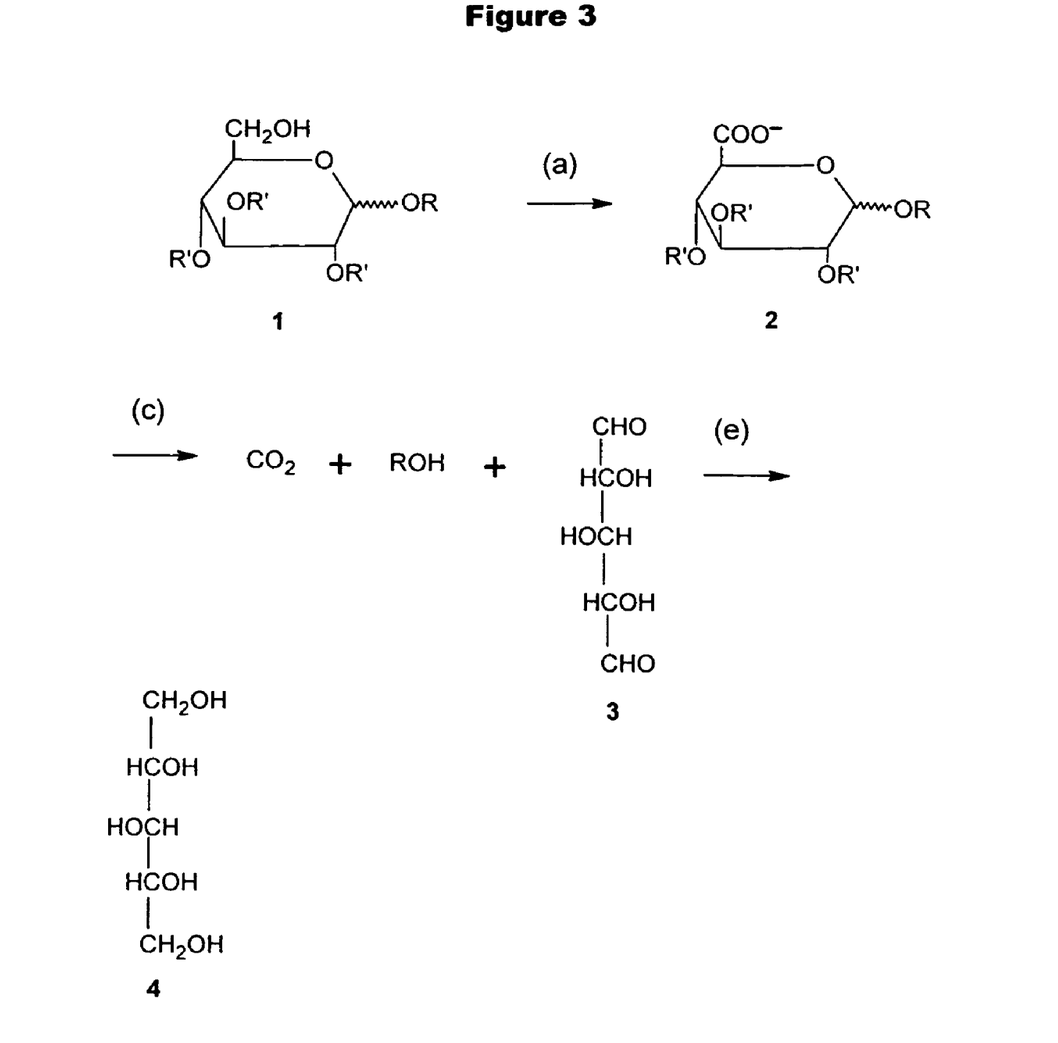
FIG. 3 shows a reaction scheme according to the process of FIG. 2.

FIG. 3 shows a detailed chemical reaction scheme for various chemical compounds that can be used according the methods for producing xylitol according to the reaction schemes of FIG. 2. The starting material or precursor material (1) may be any suitable compound that can be chemically altered to form reactant substrate (2) that undergoes electrochemical oxidative decarboxylation (c). As noted above, a suitable starting material or precursor material can comprise any D-glucuronopyranosyl group or D-fructuronofuranosyl group that is not substituted at the oxygen in the 6-position. The starting material (1), or a precursor material (if applicable) that is converted to a reactant substrate, is preferably a salt of D-glucuronic acid (1 in FIG. 2) or a glycoside, oligomer, or polymer thereof, either as a natural material or produced by oxidation. Two examples of suitable natural materials useful as a precursor material or a starting material are gluuoran and glucuronan (a naturally-occurring polymer of glucuronic acid). Other suitable starting material (1) compounds include glucosides (R=alkyl or aryl group), compounds with D-glucopyranosyl units in glycosidic linkages such as malto- or cellulo-oligo- or polysaccharides (R and/or one of the R' groups=a D-glucopyranosyl unit, the other R' groups=H), D-glucopyranosyl phosphate (R=phosphate), D-glucopyranosyl fluoride (OR=F), or sucrose (R=D-fructofuranosyl unit). The starting material (1) may have either an alpha or beta configuration at carbon number 1. Alternatively, oligo- and polysaccharides containing 2,1-linked D-fructofuranosyl units may also serve as starting materials. In another aspect, a salt of a D-fructofuranosyluronate-containing compound or a 2,1-linked oligomer or polymer thereof produced by oxidation of a 2,1-linked fructan or oligomers obtained from it also may serve as the reactant substrate of the reaction sequence.

In FIG. 3, the starting material (1) is converted to a suitable reactant substrate (2) as described above with respect to the reaction schemes of FIG. 2. In reactant substrate (2), the aglycon of the glycoside (R) is preferably a chemical moiety selected from the group consisting of: an alkyl or aryl alcohol, a sugar, and glucopyranuronosyl unit (oligo- or polyglucuronic acid) or a like protecting group for carbon 1 of the glucuronopyranosyl unit. The remaining steps in the chemical reaction scheme of FIG. 3, including the oxidative decarboxylation (c) to yield a xylitol intermediate compound (3) and the reduction hydrogenation (e) to yield the xylitol product (4), are carried out as described in the reaction schemes illustrated in FIG. 2. Preferably, the reactant substrate is a uronic acid and the xylitol intermediate (3) is a dialdehydo xylitol intermediate.

In a first preferred aspect of the first embodiment, a method of preparing xylitol comprises the following steps: providing a D-glucopyranosyl-containing starting material, oxidizing the D-glucopyranosyl-containing starting material in any suitable manner to form a reactant substrate comprising a D-glucuronopyranosyl moiety, electrochemically decarboxylating the reactant substrate containing the D-glucuronopyranosyl moiety to form a xylitol intermediate; reducing and hydrogenating the xylitol intermediate in any suitable manner to produce xylitol. Preferably, the oxidative decarboxylation is carried out by an anodic electrochemical process. Also preferably, the xylitol intermediate is a non-ionic species. In one aspect, the xylitol intermediate is D-xylo-pent-1,5-diose.

In another preferred aspect of the first embodiment, a method of preparing xylitol comprises the following steps: providing a D-glucopyranosyl-containing starting material, oxidizing the D-glucopyranosyl-containing starting material in any suitable manner to form a precursor material comprising a D-glucuronopyranosyl moiety, hydrolyzing the precursor material comprising the D-glucuronopyranosyl moiety in any suitable manner to form a reactant substrate comprising a D-glucuronic acid moiety, electrochemically decarboxylating the reactant substrate containing the D-glucuronic acid moiety to form a xylitol intermediate; reducing and hydrogenating the xylitol intermediate in any suitable manner to produce xylitol. Preferably, the oxidative decarboxylation is carried out by an anodic electrochemical process. Also preferably, the xylitol intermediate is a non-ionic species. In one aspect, the xylitol intermediate is D-xylo-pent-1,5-diose.

In a third preferred aspect of the first embodiment, a method of preparing xylitol comprises the following steps: providing a D-fructuronofuranosyl-containing starting material that is unsubstituted at the six oxygen position, oxidizing the D-fructofuranosyl-containing starting material in any suitable manner to form a reactant substrate comprising a D-fructuronofuranosyl moiety, hydrolyzing the precursor material containing the D-fructuronofuranosyl moiety, and oxidatively decarboxylating the precursor material containing the D-fructuronofuranosyl moiety to produce xylitol. Preferably, the oxidative decarboxylation is carried out by an anodic electrochemical process.

While certain preferred aspects of the first embodiment are presented with respect to particular molecular structures, many other reactant substrates, precursor materials and starting materials are also contemplated. For example, an electrochemical decarboxylation could be applied to any compound comprising uronic acid moieties to produce other precursor materials. A 2,1-linked D-fructofuranosyluronate unit, such as may be obtained by oxidation of the primary alcohol group (carbon-6 of inulin, inulin oligosaccharides, or other 2,1-linked fructan) in the same manner that compounds containing D-glucopyranosyl units are oxidized, may undergo the same fundamental series of reactions leading to a carbocation (carbonium ion) of a furan. The subsequent addition of OH and ring opening and release yields an intermediate which may be reduced to a mixture of xylitol and L-arabinitol. Isomerization of L-arabinitol yields a mixture of alditol epimers, among which is xylitol (U.S. Pat. Nos. 5,714,602 and 6,458,570, both of which are incorporated herein by reference). Xylitol may also be formed biochemically from other pentitols (EP Patent No. 421882, U.S. Pat. Nos. 6,303, 353 and 6,340,582, Japan Patent No. 2004024140).

In one aspect of the first embodiment, a method of preparing xylitol comprises the following steps: providing a D-fructuronofuranosyl-containing starting material that is unsubstituted at the 6-oxygen position, oxidizing the D-fructucopyranosyl-containing starting material in any suitable manner to form a D-fructuronofuranosyl compound, decarboxylating the precursor material to form a xylitol intermediate and D-arabinitol, and reducing the xylitol precursor to produce xylitol, along with D-arabinitol. Preferably, the oxidative decarboxylation is carried out by an anodic electrochemical process.

Xylitol Synthesis Comprising Chemical Oxidative Decarboxylation

Figure 4:
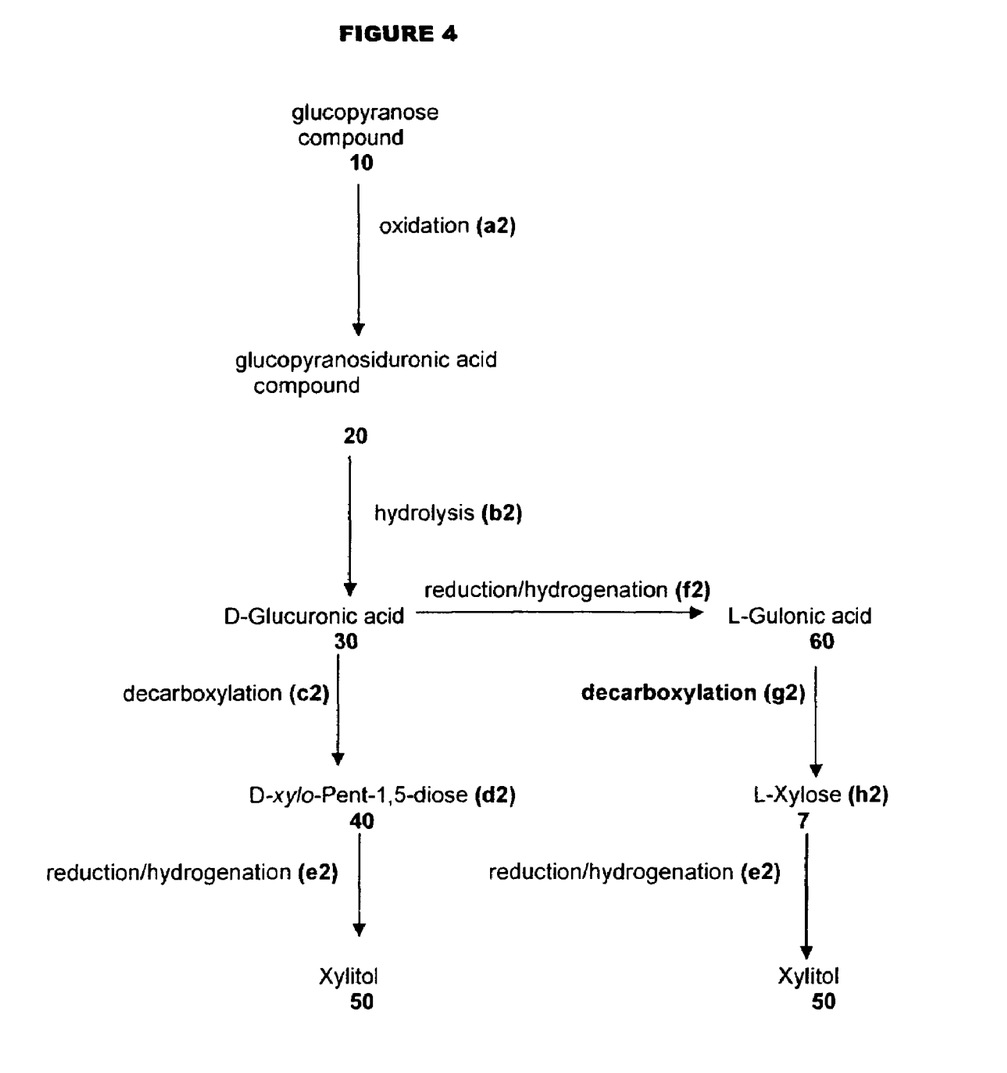
FIG. 4 shows two reaction processes for xylitol synthesis comprising chemical odixative decarboxylation processes.

In a second embodiment, shown schematically in FIG. 4, processes for producing xylitol comprise an oxidative decarboxylation step performed by one or more chemical reactions. Various chemical reactions can be used to perform the odixative decarboxylation of a reactant substrate according to the second embodiment.

Processes for preparing xylitol comprising using chemical reactions to perform a decarboxylation step are schematically presented in FIG. 4. FIG. 4 depicts two alternative processes for the production of xylitol within the second embodiment. In a first aspect, xylitol is produced from a D-glucuronic acid reactant substrate (30) that undergoes a chemical decarboxylation (c2). In a second aspect, xylitol is produced from a L-gulonic acid reactant substrate (60) that undergoes a chemical decarboxylation (g2) to form a xylitol intermediate. The xylitol intermediate produced depends on which reactant substrate is used. In the first aspect, a D-xylo-pent-1,5-diose (d2) xylitol intermediate (40) is produced. In the second aspect, a L-xylose (h2) xylitol intermediate (70) is produced. The xylitol intermediate (40), (70) can be reduced by hydrogenation reduction reaction (e2).

Any suitable starting material that can be converted to a suitable reactant substrate that can be used as a reactant substrate or a precursor material. A glucopyranose compound (10) is shown as a starting material for the processes of FIG. 4. The starting material can be oxidized (a2) to a glucopyranosiduronic acid compound (20) by any suitable oxidation reaction method, as described with respect to xylitol synthesis methods of the first embodiment, to form a precursor material or a reactant substrate. The oxidation reaction (a2) of the precursor material (10) to a glucopyranosiduronic acid precursor material (20) may be accomplished by methods known in the art, including, but not limited to: air/$O_2$ oxidation on a catalyst such as platinum, stable nitroxyl radicals (e.g., TEMPO with regeneration), transition metal ion oxidation with electrochemical regeneration, and electrochemically. Suitable oxidation reactions (a2) for use in oxidizing a D-glucopyranoyl compounds to D-glucuronopyranosyl units are described in the following references, which are incorporated herein by reference in their entirety: K. Heyns et al, "Selective catalytic oxidation of carbohydrates, employing platinum catalysts," *Advances in Carbohydrate Chemistry and Biochemistry*, 17, 169-221 (1962); T. Yamada et al., Air oxidation of cyclodextrin with a platinum catalyst," *Journal of Applied Glycoscience*, 47, 21-26 (2002); P. L. Bragd et al., "Selective oxidation of carbohydrates by 4-AcNH-TEMPO/peracid systems," *Carbohydrate Polymers*, 49, 397-406 (2002); K. Yasuda et al., "The simultaneous use of immobilized reagents for the one-pot conversion of alcohols to carboxylic acids," *Journal of the Chemical Society, Perkin Transactions*, 1, 1024-1025 (2002).

The glucopyranosiduronic acid (20) can be used as a precursor material that can be converted to a reactant substrate or to another precursor material. The glucopyranosiduronic acid (20) can be converted to the D-glucuronic acid (30) by hydrolysis (b2) of the glucopyranosiduronic acid precursor material (20). Hydrolysis (b2) of the glucopyranosiduronic acid precursor material (20) can be performed in any suitable manner, such as by using an enzyme, such as α- and/or β-glucuronosidase, or by use of an acid with heat. The glucuronic acid (30) may be separated from any non-ionic saccharides by ion-exchange chromatography.

The D-glucuronic acid (30) can serve as a reactant substrate and can undergo chemical decarboxylation (c2). Alternatively, the D-glucuronic acid (30) preferably serves as a precursor material that is subsequently reduced (f2) by a suitable dehydrogenation reaction, to form a L-gulonic acid (60) reactant substrate. A D-glucuronic acid reactant substrate (30) may be reduced by a method known in the art. Suitable hydrogenation reduction reactions involve the use of hydrogen plus a hydrogenation catalyst, for example as described above for the reduction (e2) of the xylitol intermediate (4) in FIG. 2.

A D-gulonic acid reactant substrate (30) may undergo any suitable type of chemical oxidative decarboxylation (c2) to yield a first xylitol intermediate (40) (D-xylo-pent-1,5-diose, (d2)). Similarly, L-gulonic acid reactant substrates (60) may undergo any suitable type of oxidative decarboxylation (g2) to yield a second xylitol intermediate (h2) (L-xylose). Oxidative decarboxylation reactions typically result in liberation of carbon dioxide and formation of the xylitol intermediates such as D-xylo-pent-1,5-diose (d2) or L-xylose (h2). These non-ionic xylitol intermediates (40) and (70) may be separated from unreacted starting material by anion-exchange chromatography.

The oxidative decarboxylation (c2), (g2) can be performed on a reactant substrate (30) using various chemical reactions. Examples of suitable chemical oxidative decarboxylation approaches include, but not limited to, one or more of the following: use of a transition metal ion catalyst with a primary oxidizing agent, use of a hypochlorite/hypochlorous acid, photochemical Hofer-Moest reactions, and the use of supercritical water.

In one aspect, a chemical oxidative decarboxylation is performed using hypochlorite/hypochlorous acid. Preferably, the chemical oxidatative decarboxylation is performed on reactant substrates comprising an (alpha)-hydroxy acid position, such as D-glucuronic acid or L-gulonic acid. Amides of sugar acids can also be decarboxylated from hypochloride (Hoffman degradation). The Hoffman degradation can also be used for the decarboxylation of glycuronosides. Further details on the oxidative decarboxylation of carbohydrates using hypochlorite/hypochlorous acid are found in R. L. Whistler et al, "Preparation of D-arabinose and D-glucose with hypochlorite," *Journal of the American Chemical Society*, 81, 46397 (1981), which is incorporated herein by reference.

Chemical oxidative decarboxylation can also be performed using supercritical water, for example as described by V. Di Tullio et al., "Supercritical water refining of petroleum residues and simultaneous hydrolysis-decarboxylation of waste glycerides, fats and proteins," PCT International Application Publication No. WO 2002/74881 (Int'l. Filing Date Sep. 26, 2002) (*Chemical Abstracts* 137, 265376 (2002)), which is incorporated herein by reference in its entirety.

In another aspect, a chemical oxidative decarboxylation is performed using transition metal ion catalyst such as: Fe(III), Cu(II), Ru(III), Co(II), Mn(III), Ag(I), Bi(III)/Bi(0), and complexes of them with a primary oxidizing agent such as hydrogen peroxide, hypochlorite, hypochlorite/bromide, hypobromite, chlorine dioxide, oxygen, ozone, peroxynitrite, persulfate, or bromine to regenerate the catalyst.

Preferably, the method of producing xylitol comprises performing a chemical oxidative decarboxylation using a copper transition metal ion catalyst, such as a Cu(II) catalyst, in combination with any suitable primary oxidizing agent. For example, a Ruff degradation procedure can be performed, preferably using copper ions rather than iron for the Ruff degradation of acidic sugars. Cu(I)/oxygen decarboxylation of aliphatic and (alpha)-hydroxy acids in organic solvents can be used in one aspect. In another aspect, Cu(III) salts of periodate and tellurate can be used to decarboxylate (alpha)-hydroxy acids to yield aldehydes and ketones. The Ruff degradation is described in W. Pigman et al., "The Carbohydrates," Academic Press, New York, 2nd Ed., Vol. IA (1972), Vol. IB (1980), portions of which relevant to oxidative decarboxylations of carbohydrates are incorporated herein by reference.

The chemical oxidatative decarboxylation can also be performed using a Ru(III) catalyst in combination with a suitable primary oxidizing agent described above, for example as described in Y. R. Rao et al, "Kinetics of ruthenium (III)-catalyzed oxidative decarboxylation of some aliphatic acids by ceric sulfate," Proceedings of the National Symposium on Catalysis, 4th, 341-346 (Chemical Abstracts 94, 46397 (1981)), which is incorporated herein by reference.

Alternatively, the chemical oxidatative decarboxylation can be performed using Ce(IV) compound, for example decarboxylate D-gluconic acid to yield D-arabinose. Lead (IV) acetate can also be used in decarboxylation reactions, for example for the selective cleavage of glycuronosidic linkages, as known in the art.

Various suitable transition metal ions can be used to decarboxylate a-(alpha)-hydroxy acids following a Hofer-Moest style decarboxylation mechanism. For example, chemical decarboxylation reactions can also be Kolbe/Hofer-Moest-style decarboxylation reactions performed using one or more of the following: Pb(IV), Ag(II), Mn(III), Co(III), Ce(IV) or Th(III). Other examples include the use of one or more compounds comprising a Ni(II) ion or a Ti(IV) in a Ruff degradation, compounds comprising. Other useful compounds for performing oxidative decarboxylation may include compounds comprising one or more of the following: Au(III), Pt(IV), Ir(IV), Ag(II), and Hg(II), as known in the art. For decarboxylations of pyranose compounds, preferred oxidative decarboxylation methods include the Hoffman degradation methods and methods comprising the use of Pb(IV)-containing compounds.

Photochemical versions of the Hofer-Moest reaction can also be used for oxidative decarboxylations. Photooxidation versions of the reaction employ titanium oxide (which may be doped with Fe, Cu, Ag or other metal ions) or iron (III)-porphyrin complexes. Further details of these photochemical oxidative decarboxylation methods are found in the following references, which are incorporated herein in their entirety: J. M. Hermann et al, "Photocatalytic degradation of aqueous hydroxyl-butandioic acid (malic acid) in contact with powdered and supported titania in water," Catalysis Today, 54, 131-141 (1999); P. Hanson et al., "The mechanisms of the photo-decarboxylation of alkyl- and arylmethyl-carboxylates using visible light and iron (III) tetra-(2-N-methylpyridyl) porphyrin pentachloride in aqueous solution," Journal of the Chemical Society, Perkins Transactions, 2, 2653-2568 (1998).

Referring again to FIG. 4, a first xylitol intermediate (40), shown as D-xylo-pent-1,5 diose (d2), or a second sylitol intermediate (70), shown as L-xylose (h2), can be reduced (e2) by using hydrogen and a hydrogenation catalyst to produce xylitol (50). The reduction (e2) can be performed using any suitable reaction, such as a ruthenium or nickel catalyst. For example, a reduction (e2) can be a hydrogenation reaction performed with hydrogen and a ruthenium (See WO Patent Appl. No. 2004052813, incorporated herein by reference), nickel (U.S. Pat. No. 4,008,285, incorporated herein by reference), or other hydrogenation catalysts according to known art to produce xylitol (50). In one aspect, a hydrogenation can be performed at temperatures between 70° C. and 150° C. and at pressures between 0.1 and 10 MPa H2. Alternatively, electrochemical reduction may be used (Taylor, Chemical and Metallurgical Engineering, Vol. 44 (1937) 588, which is incorporated herein by reference). In one aspect, a D-xylo-pent-1,5-ose (d2) xylitol intermediate (40) and/or L-xylose (h2) xylitol intermediate (70) may be reduced with hydrogen and a ruthenium.

After reduction (e2), xylitol (50) may be recovered from the final product by crystallization, for example as described by De Faveri et al., Journal of Food Engineering 61 (2004) 407, which is incorporated herein by reference in its entirety. L-Xylose (70) may be separated from unreacted L-gulonate salts by anion-exchange chromatography. Xylitol may be separated from L-gulonic or D-glucuronic acid by any suitable means, including ion-exchange chromatography. In one particularly preferred aspect, a L-gulonic acid in its ionized salt form is oxidized to yield L-xylose and to decarboxylate D-glucuronic acid to yield a dialdehyde, both of which products can be reduced to produce xylitol.

Figure 5:
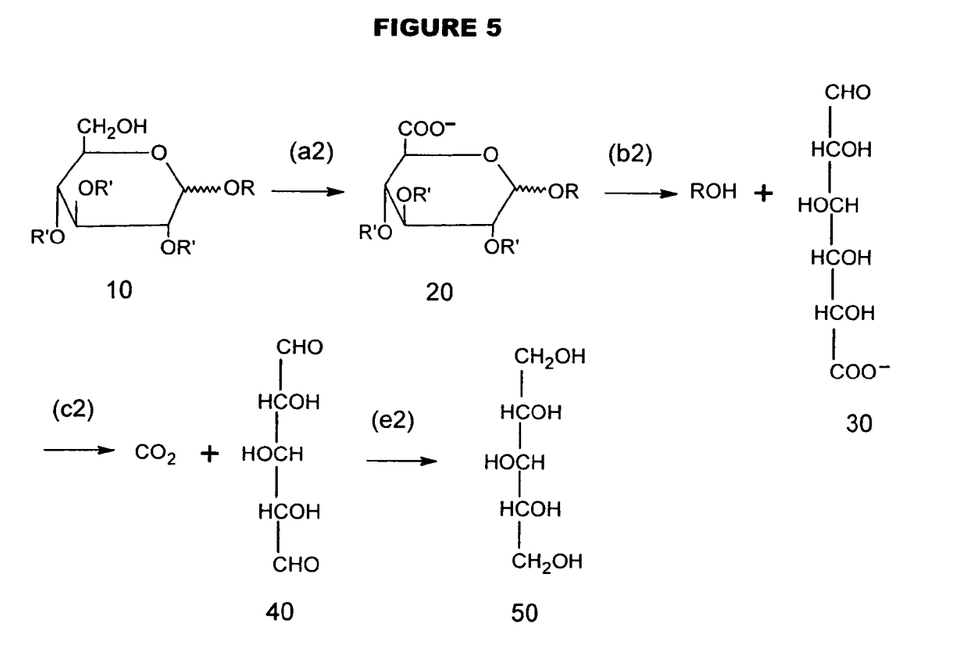
FIG. 5 shows a reaction scheme according to a first process of FIG. 4.

FIG. 5 depicts the reaction sequence described in FIG. 4 when the starting material (10) is a glycosidically linked α-D-glucopyranosyl unit or related compounds and the reactant substrate is a D-glucuronic acid (30). In FIG. 5, the starting material (10) is oxidized (a2) to precursor material (20) (e.g., a glucopyranosiduronic acid compound) which is hydrolyzed (b2) to D-glucuronic acid (30) reactant substrate. Chemical oxidative decarboxylation (c2) of D-glucuronic acid reactant substrate (30) produces a dialdehyde xylitol intermediate (40), which may be reduced to xylitol (50). Preferably, the xylitol intermediate (40) is a dialdehydo xylitol intermediate.

Figure 6:
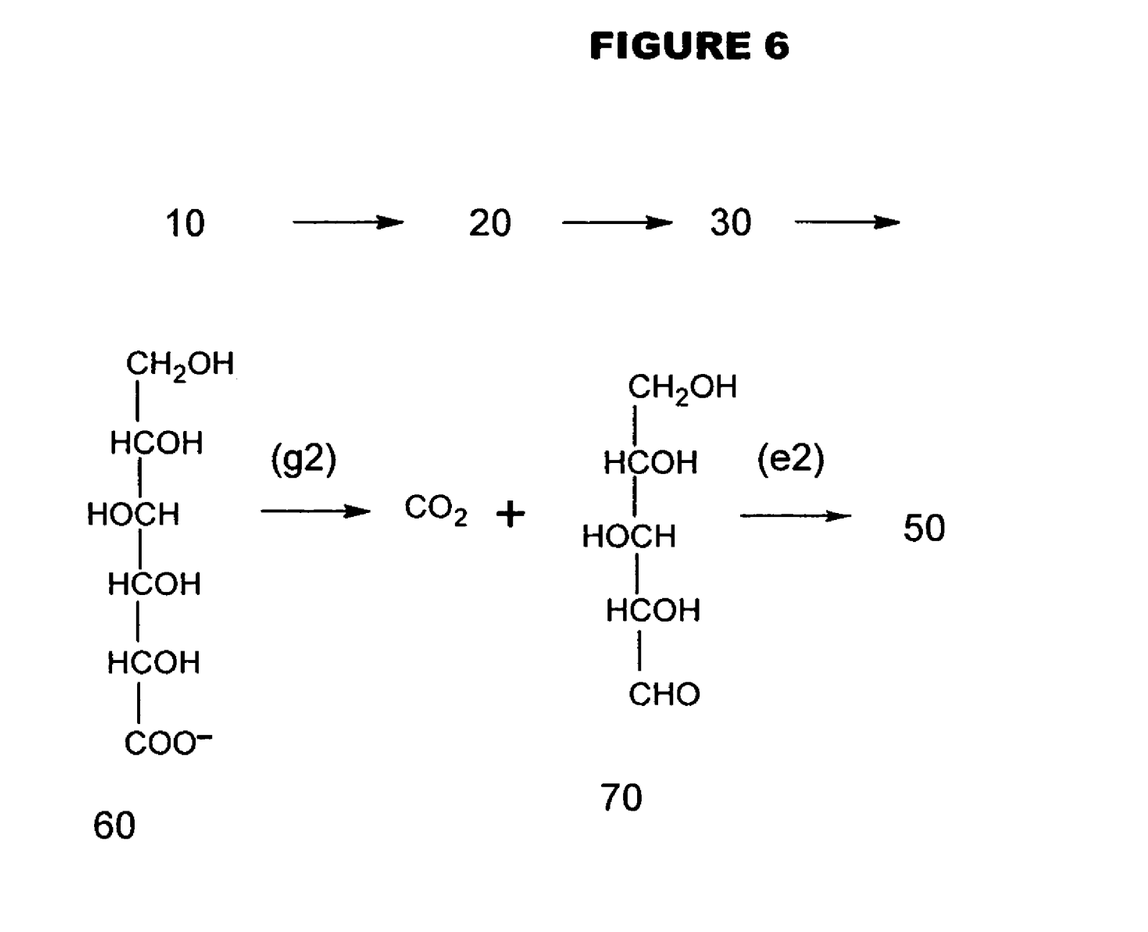
FIG. 6 shows a reaction scheme according to a second process of FIG. 4.

FIG. 6 depicts the reaction sequence of FIG. 4 when the D-glucuronic acid (30) compound (30) is a precursor material that is reduced (f2) to a L-gulonic acid (60). The L-gulonic acid (60) undergoes decarboxylation to produce a L-xylose (70) xylitol intermediate, which may be reduced (e2) to xylitol (50).

Preferably, a D-glucuronic acid compound (30) is a salt comprising sodium, potassium, ammonium, calcium, and/or magnesium salts of oligo- or poly(glucuronic acid) (degree of polymerization 2 or greater). More specifically, the D-glucuronic acid compound (30) can be a salt of D-glucuronic acid, an alkyl or aryl D-glucuronopyranoside, D-glucuronopyranose 1-phosphate, and D-glucuronopyranosyl fluoride. The reactant substrate (30) can also be a D-fructuronofuranosyl compound, optionally comprising sodium, potassium, ammonium, calcium, and/or magnesium salts of oxidized inulin or another 2,1-linked fructan. An L-gulonic acid salt (60) preferably includes at least one of the group consisting of the sodium, potassium, ammonium, calcium and/or magnesium salts of L-gulonic acid.

Referring to FIG. 5 and FIG. 6, a starting material (10), or a precursor material, may be a compound that includes glucosides (R=alkyl or aryl group), other compounds with D-glucopyranosyl units in glycosidic linkages such as malto- or cellulo-oligo- or polysaccharides (R and/or one of the R' groups=a D-glucopyranosyl unit, the other R' groups=H), D-glucopyranosyl phosphate (R=phosphate), D-glucopyranosyl fluoride (OR=F), or sucrose (R=D-fructofuranosyl unit). The hydroxyalkyl (—OR) group at the number 1 carbon of the starting material (10) can be in either an alpha or beta configuration. Optionally, the starting material (10) may be a naturally occurring glucuronan or sucrose oxidized to include a D-glucuronic acid unit. The starting material can also be obtained by oxidizing an alkyl glucoside, D-glucose 1-phosphate, or D-glucopyranosyl fluoride to the corresponding compound containing D-glucuronic acid; a starch, a dextrin, a maltodextrin, or other starch-derived material to compounds containing multiple D-glucuronic acid units; oxidizing cellulose or a cellodextrin to compounds containing multiple D-glucuronic acid units; sucrose to produce a glucuronic acid unit. The starting material also may be a naturally occurring glucuronan.

The reactant substrate (20) in FIG. 5 is preferably a D-glucuronic acid or a glycoside, oligomer or polymer thereof, or a related compound either as a natural material or produced by oxidation. The reactant substrate (60) in FIG. 6 is preferably a L-gulonic acid compound. The xylitol intermediate (40) in FIG. 5 (from the oxidative decarboxylation of D-glucuronic acid and glycosides or related compounds thereof) or the xylitol intermediate (60) in FIG. 6 (from the oxidative decarboxylation of L-gulonic acid) can be reduced (e2) to yield xylitol (50). The reduction (e2) can be carried out by any suitable method, including those described with respect to the sylitol intermediate reduction step (e) in FIG. 2 for the first embodiment.

In one aspect of the second embodiment, a method of preparing xylitol comprises the following steps: providing a D-glucopyranosyl-containing starting material, oxidizing the D-glucopyranosyl-containing starting material in any suitable manner to form a first precursor material comprising a D-glucuronopyranosyl moiety, hydrolyzing the first precursor material in any suitable manner to form a second precursor material comprising a D-glucuronic acid, reducing and hydrogenating the second precursor material in any suitable manner to form a reactant substrate comprising L-gulonic, oxidatively decarboxylating the reactant substrate comprising L-gulonic acid to produce xylitol intermediate, reducing and hydrogenating the xylitol intermediate in any suitable manner to produce xylitol. Preferably, the xylitol intermediate is L-xylose.

An alternative aspect of the second embodiment provides a method of preparing xylitol comprises the following steps: providing a D-glucopyranosyl-containing starting material, oxidizing the D-glucopyranosyl-containing starting material in any suitable manner to form a precursor material comprising a D-glucuronopyranosyl moiety, hydrolyzing the precursor material containing the D-glucuronopyranosyl moiety in any suitable manner to form a reactant substrate comprising D-glucuronic acid, oxidatively decarboxylating the reactant substrate comprising D-glucuronic acid to produce a xylitol intermediate, reducing and hydrogenating the xylitol intermediate in any suitable manner to produce xylitol. In this aspect, the xylitol intermediate is typically D-xylo-pent-1,5-diose.

Another aspect of the second embodiment provides a method of preparing xylitol comprises the following steps: providing a D-glucopyranosyl-containing starting material, oxidizing the D-glucopyranosyl-containing starting material in any suitable manner to form a precursor material comprising a D-glucopyranosiduronic moiety, hydrolyzing the precursor material containing the D-glucopyranosiduronic moiety in any suitable manner to form a reactant substrate comprising D-glucuronic acid, oxidatively decarboxylating the reactant substrate comprising D-glucuronic acid to produce a xylitol intermediate, reducing and hydrogenating the xylitol intermediate in any suitable manner to produce xylitol. In this aspect, the xylitol intermediate is typically D-xylo-pent-1,5-diose.

The methods for producing xylitol yield about 20, 30, 40, 40, 50, 60, 70, 80, 85, 90, 95 or up to 100% of the theoretical yield, more preferably at least about 40%, at least about 60%, at least about 80%, or preferably at least about 95% of theoretical yield.

Also preferably, the methods for producing xylitol consume at least about 20, 30, 40, 40, 50, 60, 70, 80, 85, 90, 95 or up to 100% of the starting material on a molar basis, and more preferably consume at least about 50%, at least about 60%, at least about 70%, at least about 80%, at least about 90%, at least about 95%, or more of the starting material on a molar basis. In some embodiments, unreacted starting material is recycled by reusing the unreacted starting material at the start of a new reaction as a starting material, precursor material as a reactant substrate.

Illustrative combinations of aspects of the embodiments are described below. Illustrative combinations of aspects of the embodiments are described below. With respect to the methods of synthesizing xylitol of the first embodiment, electrochemical oxidative decarboxylation of a reactant substrate comprising a pyranose or furanose ring structure is particularly preferred. In one aspect, reactant substrates for oxidative decarboxylation are substances comprising a D-glucuronopyranosyl group without chemical substitution at the oxygen in the 6 position of the pyranosyl ring. In another aspect, reactant substrates for oxidative decarboxylation are substances comprising a D-fructuronofuranosyl group without chemical substitution at the oxygen in the furanosyl ring. With respect to the methods of synthesizing xylitol of the second embodiment, reactions comprising the steps of hydrolysis of a compound comprising a D-glucuronopyranosyl unit, releasing free D-glucuronic acid, and subsequent reduction to L-gulonic acid are preferred. Reduction with metal ion catalysts, particularly copper (e.g., a Ruff degradation), is preferred for the reduction of D-glucuronic acid to L-gulonic acid. Several specific illustrative combinations of aspects of the first and the second embodiments are provided below.

In a first illustrative aspect, a method of producing xylitol comprises one or more of the following steps:
  a. decarboxylating a D-glucuronic compound electrochemically to produce a dialdehydoxylitol intermediate,
  b. hydrogenating the xylitol intermediate in the presence of a catalyst to produce xylitol
  c. optionally separating the xylitol intermediate from unreacted uronic acid salt or glycoside, oligomers, or polymers thereof and related compounds;
  d. optionally recycling of any unreacted starting material to step (a).

In a second illustrative aspect, a method of producing xylitol comprises one or more of the following steps:
  a. decarboxylating the D-fructuronofuranosyl acid salt or glycoside, oligomer, or polymer of it electrochemically to produce a dicarbonyl xylitol intermediate;
  b. hydrogenating the intermediate in the presence of a catalyst to produce a mixture of xylitol and D-arabinitol.
  c. optionally separating the intermediate from unreacted D-fructuronofuranosyl acid salt or glycoside, oligomers, or polymers of it; or
  d. optionally further comprising recycling of the residual starting material to step (a).

In a third illustrative aspect, a method of producing xylitol comprises one or more of the following steps:
  a. decarboxylating a salt of L-gulonic acid electrochemically to produce L-xylose.
  b. hydrogenating the L-xylose in the presence of a catalyst to produce xylitol.
  c. optionally separating the L-xylose or xylitol from unreacted L-gulonic acid salt.

d. optionally recycling of any unreacted starting material to step (a).

In a fourth illustrative aspect, a method of producing xylitol comprises the step of dissolving a uronic acid salt or glycoside thereof in a suitable water-miscible solvent, such as water, methanol, ethanol, dioxane, or acetonitrile.

In a fifth illustrative aspect, a method of producing xylitol comprises an electrochemical decarboxylation step. Preferably, an oxidative decarboxylation occurs within a electrochemical cell at an anode. More preferably, the anode comprises spectroscopic graphite, pyrolytic carbon, wax-impregnated graphite, glassy carbon, dispersed graphite, dispersed carbonaceous material, carbon cloth, coke, or platinum as a packed bed, fluidized bed, or porous anode. Also preferably, a reduction reaction occurs at a cathode within the electrochemical cell.

In a sixth illustrative aspect, a method of producing xylitol comprises the step of a catalytic hydrogenation/reduction step optionally performed using a ruthenium, Raney-nickel, or other hydrogenation catalyst.

In a seventh illustrative aspect, a method of producing xylitol comprises one or more of the following steps:
  a. reducing D-glucuronic acid to L-gulonic acid,
  b. decarboxylating a salt of L-gulonic acid produce L-xylose;
  c. hydrogenating the L-xylose in the presence of a hydrogenation catalyst to produce xylitol, optionally using a ruthenium, nickel, or other hydrogenation catalyst;
  d. optionally separating the L-xylose from unreacted L-gulonic acid; or
  e. optionally recycling of the residual L-gulonate to step (b).

The L-gulonic acid can optionally be provided in the form of its sodium, potassium, ammonium, calcium, and/or magnesium salt.

In an eighth illustrative aspect, a method of producing xylitol comprises performing a chemical oxidative decarboxylation step in one or more of the following ways:
  a. employing a transition metal ion catalyst such as Fe(III), Cu(II), Ru(III), Co(II), Mn(III), Ag(I), or Bi(III)/Bi(0);
  b. employing a complexed, transition metal ion;
  c. employing a primary oxidant, such ashydrogen peroxide, hypochlorite/hypochlorous acid, hypobromite/hypobromous acid, hypochlorite/bromide, chlorine dioxide, oxygen/air, ozone, peroxynitrite, or persulfate.
  d. employing a photoxidative decarboxylation effectuated with titanium oxide, a titanium dioxide doped with Fe, Cu, Ag or other metal ions, or a titanium oxide doped with iron (III)—porphyrin or other metal ion complexes; or
  e. employing a hypochlorite/hypochlorous acid or hypobromite/hypobromous acid.

In an ninth illustrative aspect, a method of producing xylitol comprises performing one or more of the following steps:
  a. hydrolyzing the compound containing a D-glucuronic acid unit,
  b. decarboxylating a salt of D-glucuronic acid produce a dialdehydo intermediate of xylitol, and
  c. hydrogenating the xylitol intermediate in the presence of a hydrogenation catalyst to produce xylitol;
  d. optionally separating the xylitol intermediate from unreacted uronic acid salt
  e. optionally recycling of the residual starting material to step (b).

EXAMPLES

The following examples are illustrative only, and should not be interpreted as limiting since further modifications of the disclosed embodiments will be apparent to those skilled in the art in view of this teaching. All such modifications are deemed to be within the scope of the embodiments disclosed herein.

Example 1

Electrochemical Decarboxylation of a D-Glucuronate Monohydrate Salt to Produce Xylitol Sodium D-glucuronate monohydrate (2.69 g, 0.0115 mol) was dissolved in 43 mL of methanol-water (46.2% v/v). The solution was subjected to electrolysis in a undivided cell with a graphite anode at a constant 9.99 volts for 4.31 watt-hours. The electrolyte solution was then brought to 110 mL with ethanol-water (50%) and hydrogenated by the addition of Raney Nickel and the application of hydrogen gas at 1 atmosphere at 50° C. The resulting hydrogenated syrup contained 0.87 g xylitol (50% of theoretical yield) and 1.10 g soldium L-gulonate (42% of the starting material on a molar basis).

The theoretical yield, or "% of theoretical yield" was calculated as follows: First, the molecular weights were identified as follows:
  a. Sodium D-glucuronate monohydrate 235
  b. Sodium methyl b-D-glucuronate 231
  c. Sodium L-gulonate 219
  d. Xylitol 152

Next, the calculation was performed as follows: 2.69 g of starting material is 0.0114 mol and the theoretical yield of xylitol is 0.0114×152 or 1.74 g. The actual yield was 0.87 g, which is 50% of the theoretical yield.

Example 2

Electrochemical Decarboxylation of [n] a L-Gulonate Salt to Produce Xylitol

Sodium methyl β-D-glucuronoside (2.52 g, 0.0103 mol) was dissolved in 39 mL of water. The solution was subjected to electrolysis in a undivided cell with a graphite anode at a constant 9.99 volts for 8.49 watt-hours. The electrolyte solution was then brought to 110 mL with ethanol-water (50%) and hydrogenated by the addition of Raney Nickel and the application of hydrogen gas at 1 atmosphere at 50° C. The resulting hydrogenated syrup contained 0.70 g xylitol (42% of theoretical yield).

Example 3

Electrochemical Decarboxylation of n L-Gulonate Salt to Produce Xylitol

Sodium L-gulonate (2.67 g, 0.01222 mol) was dissolved in 43 mL of methanol-water (46.2% v/v). The solution was subjected to electrolysis in a undivided cell with a graphite anode at a constant 9.99 volts for 5.32 watt-hours. The electrolyte solution was then brought to 111 mL with ethanol-water (50%) and hydrogenated by the addition of Raney Nickel and the application of hydrogen gas at 1 atmosphere at 50° C. The resulting hydrogenated syrup contained 0.87 g xylitol (47% of theoretical yield) and 1.10 g sodium L-gulonate (41% of the starting material on a molar basis).

Example 4

Cu(II) Decarboxylation of a L-Gulonate Salt to Produce Xylitol

Sodium L-gulonate (2.25 g, 0.0100 mol) was dissolved in 17 mL of water and 35 mg of copper sulfate pentahydrate was added. The pH of the solution was raised to 7.0 with sodium hydroxide (2M). 1.2 mL of 30% hydrogen peroxide was added continuously over the reaction period. The pH was maintained at 7.0 via addition of sodium hydroxide (2M). After 13 minutes, the temperature was 44° C. and the copper had precipitated as an orange suspension. The reaction solution was filtered and then brought to 110 mL with 50% ethanol-water and hydrogenated by the addition of Raney Nickel and the application of hydrogen gas at 1 atmosphere at 50° C. The resulting hydrogenated syrup contained 0.91 g xylitol (58% of theoretical yield) and 0.72 g sodium L-gulonate (32% of the starting material on a molar basis).

Example 5

Hypochlorous Acid Decarboxylation of a L-Gulonate Salt to Produce Xylitol

Sodium L-gulonate (0.244 g, $1.12 \times 10^{-3}$ mol) was dissolved in 15 mL of water, and the temperature was raised to 50° C. 1.5 mL of 13% sodium hypochlorite solution was added. 2M hydrochloric acid was added to lower the pH to 5.0. The reaction was kept at 50° C. and maintained at a pH of 5.0 via addition of 2M sodium hydroxide. After 19 min., the reaction solution was brought to 110 mL with 50% ethanol-water and hydrogenated by the addition of Raney Nickel and the application of hydrogen gas at 1 atmosphere at 50° C. The resulting hydrogenated syrup contained 0.16 g xylitol (95% of theoretical yield) and 0.004 g sodium L-gulonate (2% of the starting material on a molar basis).

While various embodiments of the invention have been described, it will be apparent to those of ordinary skill in the art that other embodiments and implementations are possible within the scope of the invention. Accordingly, the invention is not to be restricted except in light of the attached claims and their equivalents.

We claim:

1. A method of producing xylitol, comprising the steps of:
   a. electrochemically oxidatively decarboxylating a uronic acid compound to produce a dialdehydo xylitol intermediate, and
   b. hydrogenating the xylitol intermediate to produce xylitol.

2. The method of claim 1, where the uronic acid comprises a furanose or pyranose ring.

3. A method according to claim 1, wherein the uronic acid compound is dissolved in a water-miscible solvent selected from the group consisting of water, methanol, ethanol, dioxane, and acetonitrile.

4. A method of producing xylitol comprising the following steps:
   a. hydrolyzing a D-glucuronic acid compound,
   b. decarboxylating a salt of the D-glucuronic acid compound to produce a dialdehydo xylitol intermediate, and
   c. hydrogenating the dialdehydo xylitol intermediate in the presence of a hydrogenation catalyst to produce xylitol.

5. The method of claim 4 further comprising the step of separating the dialdehydo xylitol intermediate from unreacted D-glucuronic acid compound.

6. A method of producing xylitol comprising the steps of:
   a. providing a D-glucopyranosyl-containing material,
   b. oxidizing the D-glucopyranosyl-containing material to form a precursor material comprising a D-glucuronopyranosyl moiety,
   c. hydrolyzing the precursor material containing the D-glucuronopyranosyl moiety to form a reactant substrate comprising D-glucuronic acid,
   d. electrochemically oxidatively decarboxylating the reactant substrate comprising D-glucuronic acid to produce a dialdehydo xylitol intermediate; and
   e. reducing and hydrogenating the dialdehydo xylitol intermediate to produce xylitol.

7. A method of producing xylitol comprising the steps of:
   a. electrochemically decarboxylating a D-glucuronic acid compound to produce a dialdehydo xylitol intermediate; and
   b. hydrogenating the dialdehydo xylitol intermediate in the presence of a catalyst to produce xylitol.

8. The method of claim 7, further comprising the step of separating the dialdehydo xylitol intermediate from an unreacted D-glucuronic acid compound.

9. The method of claim 7, further comprising the steps of: recycling an unreacted D-glucuronic acid compound and electrochemically decarboxylating the unreacted D-glucuronic acid compound.

10. A method of producing xylitol comprising the steps of:
    a. electrochemical decarboxylation of a uronic acid compound to produce a dialdehydo xylitol intermediate, and
    b. hydrogenating the dialdehydo xylitol intermediate in the presence of a catalyst to produce a mixture of xylitol and D-arabinitol.

11. The method of claim 10, further comprising separating the dialdehydo xylitol intermediate from unreacted uronic acid compound.

12. The method of claim 11, further comprising the step of recycling of the residual uronic acid compound.

13. A method of producing xylitol comprising the steps of:
    a. providing a D-glucopyranosyl-containing starting material;
    b. oxidizing the D-glucopyranosyl-containing starting material to form a reactant substrate comprising a D-glucuronopyranosyl moiety;
    c. electrochemically decarboxylating the reactant substrate containing the D-glucuronopyranosyl moiety to form a dialdehydo xylitol intermediate;
    d. reducing and hydrogenating the dialdehydo xylitol intermediate to produce xylitol.

14. The method of claim 13, wherein the D-glucopyranosyl-containing starting material is an alkyl D-glucopyranosyl-containing starting material.

* * * * *

UNITED STATES PATENT AND TRADEMARK OFFICE
CERTIFICATE OF CORRECTION

| | | |
|---|---|---|
| PATENT NO. | : 7,598,374 B2 | Page 1 of 1 |
| APPLICATION NO. | : 11/093091 | |
| DATED | : October 6, 2009 | |
| INVENTOR(S) | : BeMiller et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1152 days.

Signed and Sealed this

Twenty-eighth Day of September, 2010

David J. Kappos
*Director of the United States Patent and Trademark Office*